US010150786B2

United States Patent
Chia et al.

(10) Patent No.: US 10,150,786 B2
(45) Date of Patent: Dec. 11, 2018

(54) SILICONE SURFACTANTS FOR EMULSION ASSAYS

(71) Applicant: Bio-Rad Laboratories, Inc., Hercules, CA (US)

(72) Inventors: Erin R. Chia, Walnut Creek, CA (US); Amy L. Hiddessen, Tracy, CA (US); Benjamin J. Hindson, Livermore, CA (US); Adam Lowe, Mountain House, CA (US); Chunxiao Han, Dublin, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 15/697,313

(22) Filed: Sep. 6, 2017

(65) Prior Publication Data

US 2017/0362258 A1 Dec. 21, 2017

Related U.S. Application Data

(62) Division of application No. 14/216,006, filed on Mar. 17, 2014, now Pat. No. 9,758,535.

(60) Provisional application No. 61/789,676, filed on Mar. 15, 2013.

(51) Int. Cl.
| | |
|---|---|
| *C12Q 1/68* | (2018.01) |
| *C08G 18/08* | (2006.01) |
| *C07F 7/18* | (2006.01) |
| *C08G 77/46* | (2006.01) |
| *C08G 77/50* | (2006.01) |
| *C08L 83/12* | (2006.01) |
| *C08L 83/14* | (2006.01) |
| *G01N 33/543* | (2006.01) |

(52) U.S. Cl.
CPC ............ *C07F 7/1804* (2013.01); *C07F 7/184* (2013.01); *C08G 77/46* (2013.01); *C08G 77/50* (2013.01); *C08L 83/12* (2013.01); *C08L 83/14* (2013.01); *G01N 33/5436* (2013.01)

(58) Field of Classification Search
CPC .................................................. C07F 7/1804
USPC .......................................... 435/6.1; 521/122
See application file for complete search history.

(56) References Cited

U.S. PATENT DOCUMENTS

| | | | |
|---|---|---|---|
| 5,041,468 A | 8/1991 | Budnik et al. | |
| 5,883,142 A | 3/1999 | Chojnacki et al. | |
| 6,512,015 B1 * | 1/2003 | Elms ................. | B01D 19/0404 516/117 |
| 6,576,623 B1 | 6/2003 | Nakanishi et al. | |
| 7,575,865 B2 * | 8/2009 | Leamon ................ | B01L 3/5027 435/6.1 |
| 9,758,535 B2 | 9/2017 | Chia et al. | |
| 2005/0002976 A1 | 1/2005 | Wu | |
| 2007/0242105 A1 | 10/2007 | Srinivasan et al. | |
| 2008/0004436 A1 | 1/2008 | Tawfik et al. | |
| 2008/0262103 A1 | 10/2008 | Stork et al. | |
| 2009/0117286 A1 | 5/2009 | Ishikawa | |
| 2009/0292015 A1 | 11/2009 | Zhang et al. | |
| 2011/0319581 A1 | 12/2011 | Yamaguchi et al. | |
| 2012/0027704 A1 | 2/2012 | Henning et al. | |
| 2013/0035408 A1 | 2/2013 | Knott et al. | |
| 2014/0356289 A1 | 12/2014 | Bayley et al. | |

FOREIGN PATENT DOCUMENTS

EP 1114635 * 6/2000

OTHER PUBLICATIONS

Nakano et al. (Journal of Biotechnology, 102, 2003, 117-124).*
Liu ( Elaissari , Ed. Colloidal Biomolecules, Biometric, and biomedical Applications (CRC Press), Chapter II pp. 309-328, 2003).*
Copenheaver, Blaine R., Authorized Officer, International Searching Authority/US, "International Search Report" in connection with related International Application No. PCT/US2014/030374, dated Oct. 28, 2014, 4 pgs.
Copenheaver, Blaine R., Authorized Officer, International Searching Authority/US, "Written Opinion of the International Searching Authority" in connection with related International Application No. PCT/US2014/030374, dated October 28, 2014, 8 pgs.
Dalet, Pierre, Examiner, European Patent Office, "Extended European Search Report" in connection with related European Patent App. No. 14762805.1-1301, dated Jul. 11, 2016, 10 pgs.
Dalet, Pierre, Examiner, European Patent Office, "Communication Pursuant to Article 94(3) EPC" in connection with related European Patent App. No. 14762805.1-1301, dated Aug. 3, 2017, 5 pgs.
Kuo, Alex C. M., "Poly(dimethylsiloxane)", James E. Mark Ed., in Polymer Data Handbook (Oxford Univ. Press), Ch. 89, Nov. 5, 2009, pp. 411-435.
Lewis, Larry N. et al., "Platinum Catalysts Used in the Silicones Industry", Platinum Metals Review, 1997, vol. 41, No. 2, pp. 66-75.
Miao, Qian Jiang et al., "Silica-supported Karstedt-type catalyst for hydrosilylation reactions", Catalysis Communications, vol. 4, 2003, pp. 637-639.

* cited by examiner

*Primary Examiner* — Jezia Riley
(74) *Attorney, Agent, or Firm* — Kolisch Hartwell, P.C.

(57) ABSTRACT

System, including methods and compositions, for making and using emulsions that include a silicone oil and a silicone surfactant. The emulsions may include aqueous droplets disposed in a continuous phase that includes a silicone oil and a silicone surfactant. The aqueous droplets may contain an analyte, optionally at partial occupancy, and/or a luminescent (e.g., photoluminescent) reporter. An assay of the analyte may be performed with the droplets. In some cases, signals may be detected from the droplets, and a characteristic of the analyte, such as an analyte level or activity, may be determined based on the signals.

11 Claims, No Drawings

SILICONE SURFACTANTS FOR EMULSION ASSAYS

CROSS-REFERENCES TO PRIORITY APPLICATIONS

This application is a divisional of U.S. patent application Ser. No. 14/216,006, filed Mar. 17, 2014, and now U.S. Pat. No. 9,758,535, which, in turn, is based upon and claims the benefit under 35 U.S.C. § 119(e) of U.S. Provisional Patent Application Ser. No. 61/789,676, filed Mar. 15, 2013. Each of these priority applications is incorporated herein by reference in its entirety for all purposes.

CROSS-REFERENCES TO OTHER MATERIALS

This application incorporates by reference in their entireties for all purposes the following materials: U.S. Pat. No. 7,041,481, issued May 9, 2006; U.S. Patent Application Publication No. 2010/0173394 A1, published Jul. 8, 2010; U.S. Patent Application Publication No. 2011/0217712 A1, published Sep. 8, 2011; and Joseph R. Lakowicz, PRINCIPLES OF FLUORESCENCE SPECTROSCOPY (2$^{nd}$ Ed. 1999).

INTRODUCTION

An emulsion is a mixture of two or more liquids that are normally immiscible (nonmixable or unblendable). Typically, one liquid, referred to as the dispersed phase, is dispersed into the other liquid, referred to as the continuous phase. Emulsions hold substantial promise for revolutionizing high-throughput assays, as emulsification techniques can create thousands, millions, or even billions of discrete aqueous droplets from a single sample. The resulting aqueous droplets, due to their isolation from each other within an immiscible continuous phase, can function as independent reaction chambers for biochemical reactions. Significantly, even a small aqueous sample can be partitioned into a vast number of droplets. For example, an aqueous sample with a volume of 200 microliters can be dispersed into approximately four million droplets, each having a volume of 50 picoliters. In this way, individual biological components (e.g., cells, nucleic acids, proteins, etc.) can be manipulated, processed, and studied discretely in a massively high-throughput manner.

Emulsions for assays are often formulated to have a continuous phase that includes a perfluorinated oil and a perfluorinated surfactant. The use of such a fluorophilic continuous phase around droplets can provide a permissive surrounding environment for certain biochemical reactions, such as PCR amplification, to occur in the droplets.

However, emulsions containing perfluorinated oil can suffer from various problems. For example, aqueous droplets are typically buoyant in perfluorinated oil, which can create problems during droplet manipulation. The buoyant droplets may be more likely to be damaged by exposure to air above the emulsion, particularly when heated. Also, such emulsions may require removal of excess oil below the droplets to position the droplets closer to a heat source. Furthermore, the droplets may be difficult to stabilize for heat treatment, such as thermocycling to promote amplification, and may be difficult to singulate prior to detection.

SUMMARY

The present disclosure provides a system, including methods and compositions, for making and using emulsions that include a silicone oil and a silicone surfactant. The emulsions may include aqueous droplets disposed in a continuous phase that includes a silicone oil and a silicone surfactant. The aqueous droplets may contain an analyte, optionally at partial occupancy, and/or a luminescent (e.g., photoluminescent) reporter. An assay of the analyte may be performed with the droplets. In some cases, signals may be detected from the droplets, and a characteristic of the analyte, such as an analyte level or activity, may be determined based on the signals.

DETAILED DESCRIPTION

The present disclosure provides a system, including methods and compositions, for making and using emulsions that include a silicone oil and a silicone surfactant. The emulsions may include aqueous droplets disposed in a continuous phase that includes a silicone oil and a silicone surfactant. The aqueous droplets may contain an analyte, optionally at partial occupancy, and/or a luminescent (e.g., photoluminescent) reporter. An assay of the analyte may be performed with the droplets. In some cases, signals may be detected from the droplets, and a characteristic of the analyte, such as an analyte level or activity, may be determined based on the signals.

A composition is provided. The composition may comprise a continuous phase that includes a silicone oil and a silicone surfactant, and aqueous droplets disposed in the continuous phase. The droplets may include an analyte at partial occupancy.

A method of performing an assay is provided. In the method, an emulsion may be formed that includes droplets disposed in a continuous phase. The continuous phase may include a silicone oil and at least one silicone surfactant. Data related to an analyte disposed in the dispersed droplets may be collected.

The system may have substantial advantages. The emulsion may prevent a droplet-air interface from forming because the droplets of the emulsion may be denser than the oil, which causes the droplets to be positioned below any excess oil in a PCR tube or plate. The droplets may be stable to thermocycling during PCR without the need for a protein skin around each droplet. Also, the droplets may sink, which allows the droplets to be packed readily prior to detection or other manipulation, affording more control over droplet transport in a droplet reader (or other device for droplet manipulation), and potentially avoiding a need for a focusing fluid in a droplet reader (or other device for droplet manipulation).

Further aspects of the present disclosure are presented in the following sections: (I) oil phase, (II) aqueous phase, (III) detection of signals from droplets, and (IV) examples.

I. Oil Phase

At least one silicone oil may be used to form the emulsion. The oil may form at least a majority of the continuous phase of the emulsion. The oil may have a low viscosity, such as less than about 10, 5, or 2 centistokes, or about one or less centistoke. The oil may be non-volatile and/or may have a density less than water. A silicone oil, as used herein, includes one or more component compounds having a polysiloxane backbone with organic side chains. That is, the backbone of a silicone oil includes a chain of alternating silicon and oxygen atoms (—Si—O—Si—O—Si—), where the silicon atoms are substituted by various hydrocarbon moieties.

A variety of silicone oils, and blends of silicone oils, may be suitable for use as a continuous phase for the purposes of the present invention. One exemplary silicone oil that may be a suitable continuous phase, or a component of a continuous phase, is a trisiloxane oil, such as octamethyl trisiloxane. Alternatively, one or more components of the continuous phase may be a polydimethylsiloxane (PDMS) polymer. In one preferred embodiment of the invention, the continuous phase includes a PDMS silicone oil having a relatively low kinematic viscosity (the ratio of dynamic viscosity to density) of about 0.1 to about 10 cSt, more preferably about the silicone oil is a 5 cSt PDMS.

The stability of an aqueous-silicone oil emulsion may be enhanced by the addition of a surfactant (amphiphile). However, some surfactants that provided good emulsion characteristics when used with carbon-based oils have been found to provide less satisfactory results when used in combination with silicone oils. Silicone surfactants may be used to stabilize the aqueous-silicone oil emulsion without suffering from the disadvantages of previously used surfactants.

At least one silicone surfactant may be included in the emulsion, generally as part of the oil phase. The surfactant may be heat stable, that is, stable to heating to a temperature of at least about 70° C., 80° C., 90° C., 100° C., or 110° C. for at least about 1, 2, 10, 30, 60, 120, or 180 minutes, among others. The surfactant may be biocompatible, biologically inert, and/or compatible with one or more chemical reactions, such as enzyme-catalyzed reactions. For example, the surface may be compatible with amplification (i.e., may not inhibit amplification substantially), such as by the polymerase chain reaction, in droplets of the emulsion. The surfactant collectively, or one or more surfactants individually, may be present at any suitable concentration in the continuous phase or in the oil before the emulsion is formed. Exemplary concentrations that may be suitable include about 0.1% to 10%, 0.2% to 5%, 0.5% to 2%, or about 1% by weight, among others.

The silicone surfactant may be described by the following general formula:

[SILICONE BACKBONE][ALKYL]$_x$ [POLYETHER]$_y$[POLYSILOXANE]$_z$ where x is 0-5, y is 1-35, and z is 2-50.

In the above general formula, the SILICONE BACKBONE moiety corresponds to a polysiloxane chain having a repeating silicon-oxygen structure substituted by alkyl substituents, having the formula:

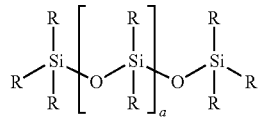

Here, a is 5-500, and each R moiety is hydrogen or an alkyl substituent, which may be the same or different, although each R moiety is typically a lower alkyl group having 1-6 carbons. Preferably, the silicone chain is substantially completely substituted by methyl groups, and the resulting silicone chain is a polydimethylsiloxane (PDMS) polymer.

The silicone backbone moiety may be further substituted by one or more additional substituents, represented in the general formula by the moieties ALKYL, POLYETHER, and POLYSILOXANE. The particular nature and number of the additional substituents may be selected to tailor the hydrophobicity and/or hydrophilicity of the surfactant, and thus to fine-tune the utility of the surfactant for stabilizing a particular aqueous/silicone oil emulsion composition. For example, the silicone backbone chain of the surfactant may be further substituted by one or more hydrophilic moieties, where the hydrophilic moiety is selected to confer enhanced hydrophilicity on the surfactant. The silicone backbone may be substituted by 1-5 hydrophilic moieties, which may be the same or different.

An example of an appropriate hydrophilic moiety is a POLYETHER moiety, such as an organic polyether chain. The organic polyether may be a linear alkyl that incorporates a plurality of bridging oxygen atoms. For example, the hydrophilic moiety may be a polyethylene glycol (PEG) moiety or a polypropylene glycol moiety. In one embodiment, the hydrophilic moiety includes a polyethylene glycol (PEG) moiety having the formula:

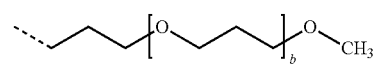

Here, b is 5-300, or more typically b is 15-100. In some embodiments, the hydrophilic moiety may be an organic polyether that is itself further substituted by an inorganic polysiloxane.

Where a hydrophilic moiety is a POLYSILOXANE moiety, it may include an inorganic polysiloxane that is optionally substituted one or more times by alkyl having 1-carbons. In one example, the inorganic polysiloxane side chain is a polydimethylsiloxane (PDMS) chain, such as, for example, a polysiloxane substituent having the formula:

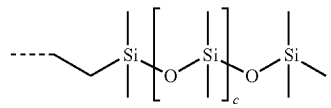

Here, c is 2-100. Alternatively, the polysiloxane moiety may include a branched polysiloxane chain, such as a secondary polysiloxane having the formula:

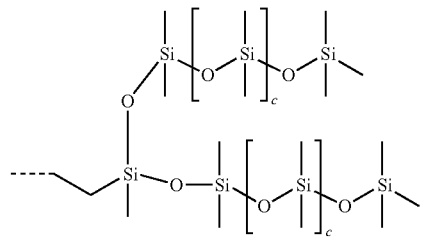

Here, each c is independently 2-100. In yet another alternative, the polysiloxane moiety may include a tertiary branched polysiloxane chain, such as, for example, a hydrophilic moiety having the formula:

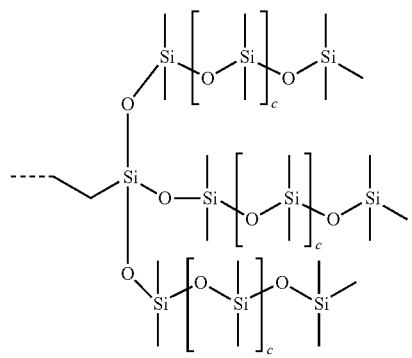

Here, each c is independently 2-100. A polysiloxane substituent may therefore be described by the formula:

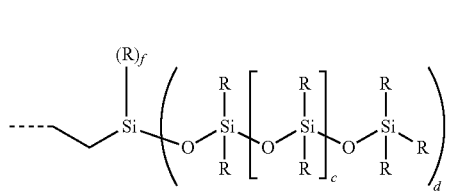

Here, each R is hydrogen or alkyl having 1-6 carbons, d is 1-3, f is (3-d), and each c is independently 2-100. Each polysiloxane moiety may be derivatized by one or more alkyl groups having 1-6 carbons, for example, at the side chain terminus.

Alternatively or in addition, the silicone backbone chain may be substituted by one or more hydrophobic moieties, where the hydrophobic moiety is selected to confer enhanced hydrophobicity on the surfactant. The silicone backbone chain may be substituted by 1-5 hydrophobic moieties, which may be the same or different. Typically, the hydrophobic moiety, if present, is an ALKYL moiety, which includes a linear alkyl side chain having 8-14 carbons.

The silicone surfactant may have any suitable structure, including a comb structure, a di-block structure, a tri-block structure, a zwitterionic structure, an X block structure, a Y block structure, or a combination thereof, among others. In some cases, the silicone surfactant may include the specific surfactants ABIL® EM 90 or ABIL® EM 180, and/or one or more of Surfactants A-F shown below:

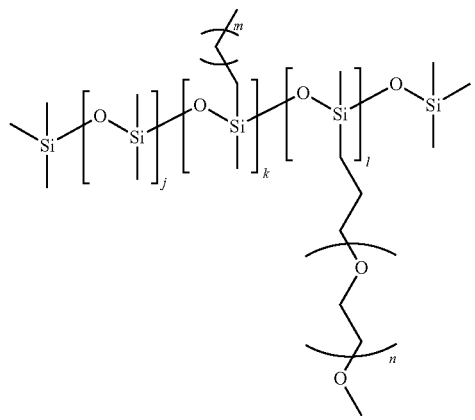

where: $j \sim 100\text{-}200$
$k \sim 2\text{-}5$
$l \sim 1\text{-}5$
$m \sim 8\text{-}14$
$n \sim 15\text{-}50$ Surfactant A

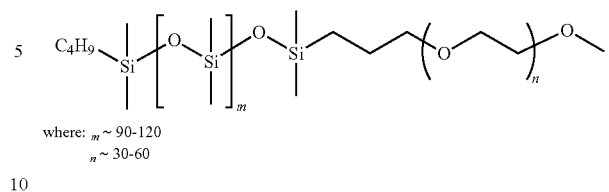

where: $m \sim 90\text{-}120$
$n \sim 30\text{-}60$

Surfactant B

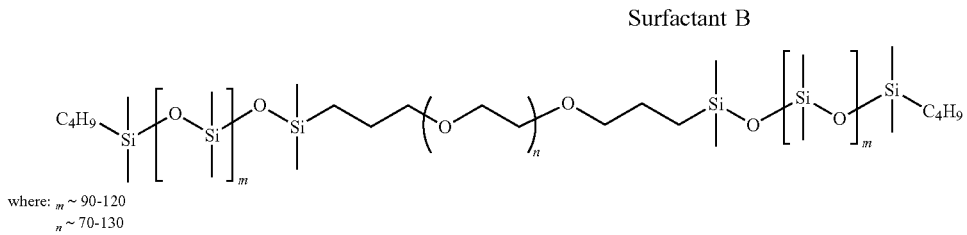

where: $m \sim 90\text{-}120$
$n \sim 70\text{-}130$

Surfactant C

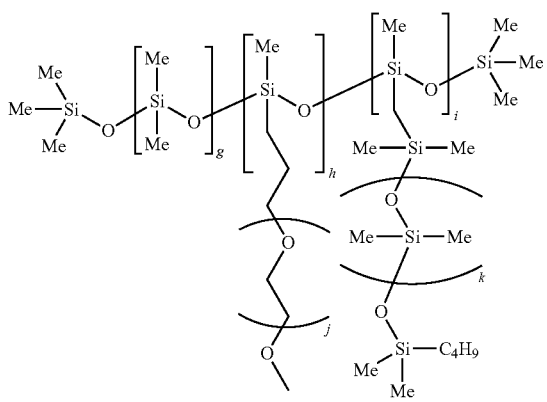

wherein
  each g is independently 5-200;
  each h is independently 1-5;
  each i is independently 1-5;
  each j is independently 15-50; and
  each k is independently 2-100.

Surfactant D

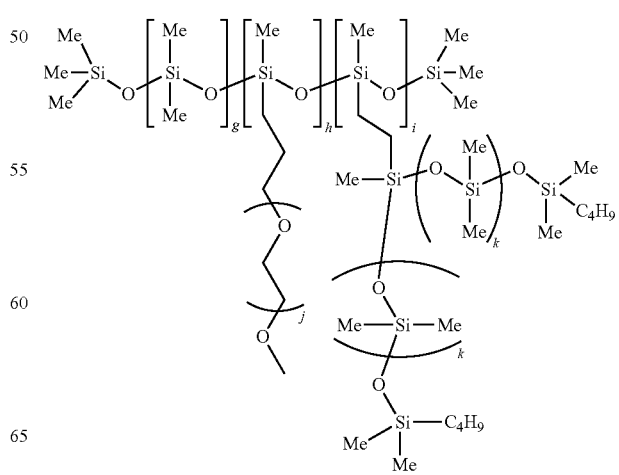

wherein
  each g is independently 5-200;
  each h is independently 1-5;
  each i is independently 1-5;
  each j is independently 15-50; and
  each k is independently 2-100.

Surfactant E

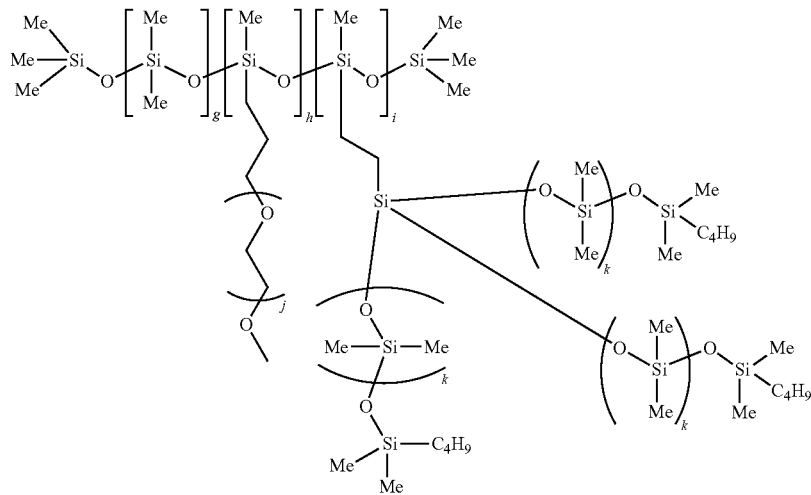

wherein
  each g is independently 5-200;
  each h is independently 1-5;
  each i is independently 1-5;
  each j is independently 15-50; and
  each k is independently 2-100.

Surfactant F

In one exemplary and preferred embodiment, the silicone surfactant may have the structure

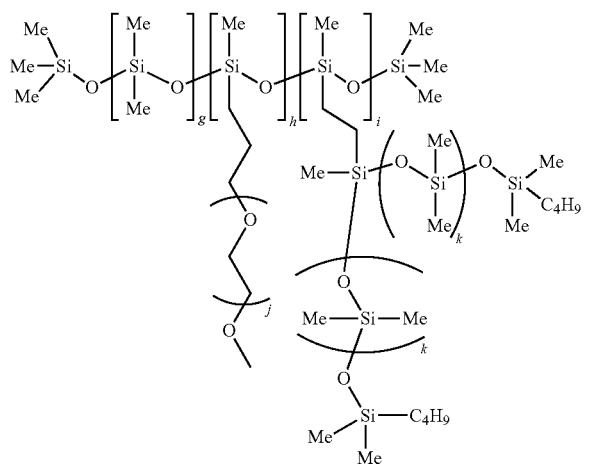

wherein
  each g is 10-25;
  each h is independently 1-3;
  each i is independently 2-4;
  each j is independently 15-20; and
  each k is independently 10-50.

In some cases, the emulsion, the continuous phase, and/or an oil composition used to prepare the emulsion, may include a silicone resin solution, for example such as XIAMETER® RSN-0749, also known as DOW CORNING® 749 FLUID, and optionally at least one silicone surfactant as described above. Alternatively, or in addition, the emulsion, continuous phase, and/or oil composition used to prepare the emulsion may include a silicone resin solution such as GP-422, available from GENESEE POLYMERS CORPORATION (Burton, Mich.). The silicone resin solution may be present at any suitable concentration, such as a concentration of about 0.1% to 10%, 0.2% to 5%, 0.5% to 2%, or about 1% by weight, among others.

In some cases, the emulsion, the continuous phase, and/or an oil composition used to prepare the emulsion, may include decamethylcyclopentasiloxane, and/or octamethylcyclotetrasiloxane, which may be present at any suitable concentration, such as a concentration of about 0.0.5% to 5%, 0.1% to 2.5%, 0.25% to 1%, or about 0.5% by weight, among others.

In some cases, the emulsion, the continuous phase, and/or an oil composition used to prepare the emulsion, may include trimethylsiloxysilicate (TSS). The TSS may be present at any suitable concentration, such as a concentration of about 0.0.5% to 5%, 0.1% to 2.5%, 0.25% to 1%, or about 0.5% by weight, among others.

A variety of silicone-based surfactants may be designed and prepared via the modification of existing carbon-based surfactants through the substitution of one or more of the hydrocarbon backbone chains and/or polyether side chains with a corresponding polysiloxane chain. The details of the geometry and chain length of the polydimethylsiloxane backbone and side chains could be readily tailored to meet the particular demands of the particular emulsion system in which the surfactant is used (or intended to be used).

Further aspects of making and using emulsions, and compositions thereof, are disclosed in the documents listed above under Cross-References, which are incorporated herein by reference.

II. Aqueous Phase

The emulsion may contain aqueous droplets formed from a continuous aqueous phase. The droplets may be monodisperse. The droplets may include, and/or may be formed with an aqueous phase including, an aqueous surfactant. The droplets also may include at least one analyte to be characterized in a droplet-based assay. The analyte may be present at partial occupancy, such that one or more (e.g., a plurality) of the droplets contain no copies of the analyte, one or more (e.g., a plurality) of the droplets may contain a single copy (only one copy) of the analyte, and, optionally, yet one or more of the droplets (e.g., the rest of the droplets) may contain two or more copies of the analyte. The term "partial occupancy" is not restricted to the case where there is no more than one copy of a particular analyte in any droplet. Droplets containing an analyte at partial occupancy may, for example, contain an average of more than, or less than, about one copy, two copies, or three copies, among others, of the analyte per droplet when the droplets are provided or formed. Copies of an analyte may have a random distribution among the droplets, which may be described as a Poisson distribution. Exemplary analytes include a biological material, such as a cell, a viral particle, an organelle, a nucleic acid target or template, a protein, an amino acid, a lipid, a carbohydrate, a hormone, a receptor, a ligand, a metabolite, a catabolite, an ion, or the like. The analyte may be characterized in the droplets to determine any suitable characteristic, such as a qualitative level (present/absent), a quantitative level or concentration, an activity, or any combination thereof, among others.

The aqueous droplets may include a reporter. The reporter may be or include a dye, which in turn may include a luminophore (e.g., a fluorophore). The reporter may be configured to interact, associate, or bind to the analyte, a reaction product representing the analyte, or the like. In any event, the reporter may be configured to report the occurrence and/or extent of a reaction, such as a chemical reaction in the droplets. Alternatively, or in addition, the reporter may report pH, a change in cellular ion concentration, cellular activity or death, protein function, viscosity, temperature, etc. Exemplary reporters for nucleic acid amplification include a dye-labeled probe, a generic reporter (e.g., an intercalating dye), or the like. In some cases, a signal may be detected by direct detection of droplets without involvement of a reporter.

The droplets may contain all necessary components to report a characteristic or activity occurring in the droplets, or additional materials may be delivered to the droplets during droplet use. In some cases, the aqueous droplets may contain a reaction mixture to perform a chemical reaction in the droplets. The reaction may be an enzyme-catalyzed reaction, and the droplets may contain at least one enzyme.

Further aspects of aqueous droplets and suitable contents of aqueous droplets are disclosed in the documents listed above under Cross-References, which are incorporated herein by reference.

III. Detection of Signals from Droplets

Signals may be detected from the droplets. The signals may be detected with the droplets moving or disposed in a one-dimensional array, a two-dimensional array, or a three-dimensional array, among others. Each signal may represent an electrical characteristic of the droplets, a thermal change, a pH, or detected light (e.g., luminescence (intensity, lifetime, polarization, energy transfer (e.g., FRET), etc.), absorbance, reflectivity, methods of direct detection, not involving reporters, etc.), among others. The signals may represent light detected from the droplets, such as light emitted in response to irradiation with excitation light. One or more signals may be detected from each of a plurality of the droplets. The signals may be detected from the droplets serially, such as while the droplets flow past a detector, in parallel, such as by imaging the droplets or with parallel flow channels (e.g., with a multi-channel singulator), laser scanning, or a combination thereof, among others. The signals may be processed to quantitatively or qualitatively determine a characteristic of the analyte and/or the droplets.

The term "luminescence" means emission of light that cannot be attributed merely to the temperature of the emitting body. Exemplary forms of luminescence include photoluminescence, chemiluminescence, electroluminescence, or the like. A "luminophore" is any atom or associated group of atoms capable of luminescence. Photoluminescence is any luminescence produced in response to irradiation with excitation light and includes fluorescence, phosphorescence, etc. Accordingly, a luminophore may be a fluorophore or a phosphor, among others.

Further aspects of signal detection from droplets, signal processing, and assays that can be performed with emulsions are disclosed in the documents listed above under Cross-References, which are incorporated herein by reference.

IV. Examples

The following examples, presented as a series of numbered paragraphs, describe selected aspects of silicone surfactants, emulsions containing silicone surfactants, and methods of using such emulsions in droplet-based assays. These examples are intended for illustration only and should not limit the entire scope of the present disclosure.

1. A silicone surfactant having the formula:

where x is 0-5, y is 1-35, and z is 2-50.

2. The silicone surfactant of paragraph 1, wherein SILICONE BACKBONE has the formula:

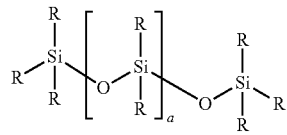

wherein a is 5-500, and each R moiety is independently hydrogen or an alkyl having 1-6 carbons.

3. The silicone surfactant of paragraph 1, wherein ALKYL is an alkyl moiety having 8-14 carbons.

4. The silicone surfactant of paragraph 1, wherein POLYETHER is an organic polyether side chain.

5. The silicone surfactant of paragraph 4, wherein POLYETHER has the formula

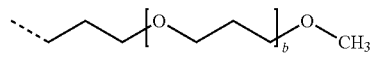

wherein b is 5-300.

6. The silicone surfactant of paragraph 1, wherein POLYSILOXANE is an inorganic polysiloxane moiety.

7. The silicone surfactant of paragraph 6, wherein POLYSILOXANE is a polydimethylsiloxane side chain.

8. The silicone surfactant of paragraph 6, wherein POLYSILOXANE has the formula:

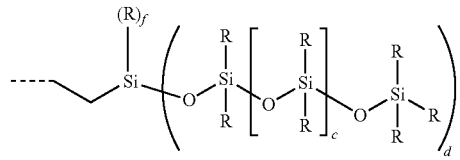

wherein each R is independently hydrogen or alkyl having 1-6 carbons, each c is independently 5-100, d is 1-3, and f is (3-d).

9. The silicone surfactant of paragraph 1, having the formula

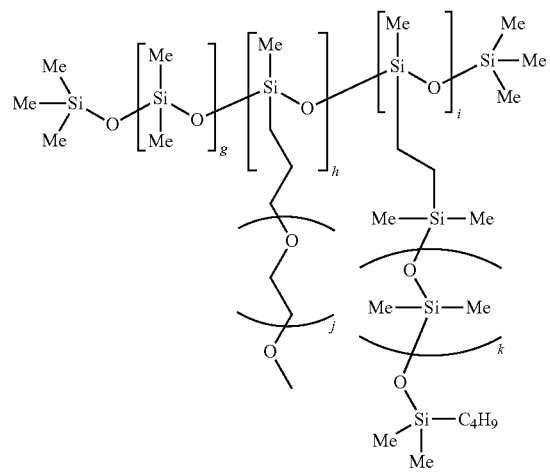

wherein
  each g is independently 5-200;
  each h is independently 1-5;
  each i is independently 1-5;
  each j is independently 15-50; and
  each k is independently 2-100.

10. The silicone surfactant of paragraph 1, having the formula

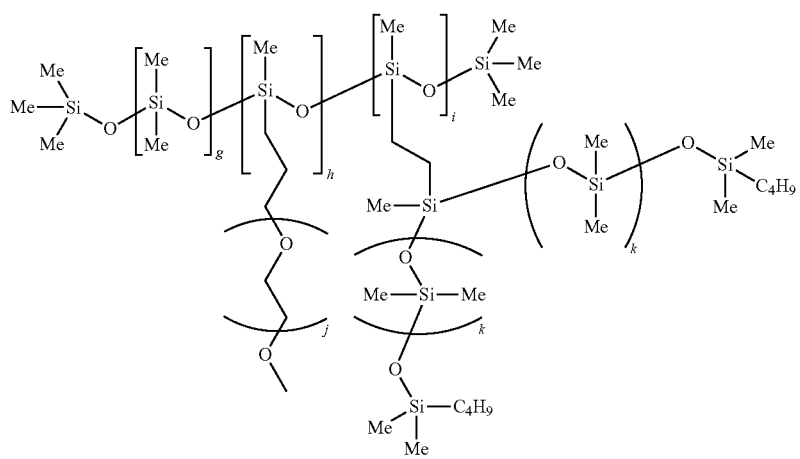

wherein
  each g is independently 5-200;
  each h is independently 1-5;
  each i is independently 1-5;
  each j is independently 15-50; and
  each k is independently 2-100.

11. The silicone surfactant of paragraph 1, having the formula

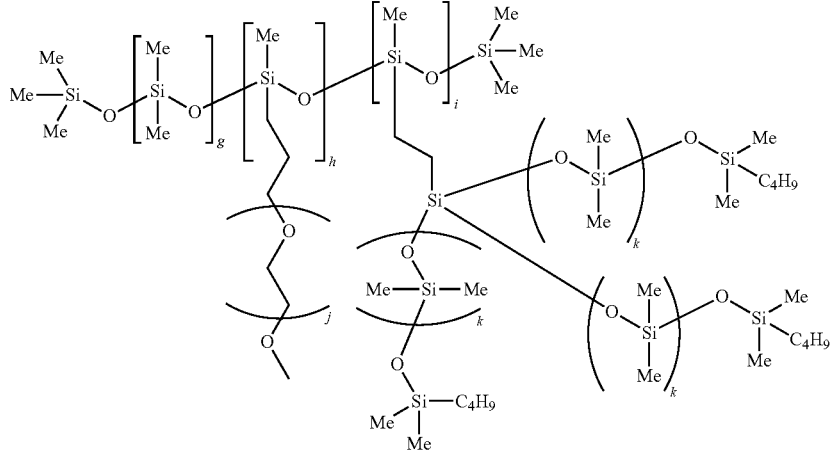

wherein
each g is independently 5-200;
each h is independently 1-5;
each i is independently 1-5;
each j is independently 15-50; and
each k is independently 2-100.

12. A composition comprising at least one silicone surfactant according to one of paragraphs 1-11.

13. The composition of paragraph 12, wherein the composition is an emulsion.

14. The composition of paragraph 12 or 13, wherein the composition includes a silicone oil.

15. The composition of paragraph 14, wherein the silicone oil includes one or more of octamethyl trisiloxane and a 5 cSt PDMS.

16. The composition of any one of paragraphs 12-15, wherein the silicone surfactant is present in the composition at a concentration of 0.1% to 10% in an oil phase.

17. A composition comprising: (A) a continuous phase including a silicone oil and a silicone surfactant; and (B) aqueous droplets disposed in the continuous phase, the droplets including an analyte at partial occupancy.

18. The composition of paragraph 17, wherein the silicone surfactant is a silicone surfactant according to one of paragraphs 1-11.

19. The composition of paragraph 17, wherein the aqueous droplets include a photoluminescent reporter.

20. The composition of one of paragraphs 17-19, wherein the analyte is a nucleic acid.

21. A method of performing an assay, comprising: (A) forming an emulsion including droplets disposed in a continuous phase that includes a silicone oil and at least one silicone surfactant according to one of paragraphs 1-11; and (B) collecting data related to an analyte disposed in the droplets.

22. The method of paragraph 21, wherein the analyte is a biomaterial.

23. The method of paragraph 21, wherein the analyte is a nucleic acid.

24. The method of any one of paragraphs 21 to 23, wherein copies of the analyte are present in the droplets at partial occupancy when the emulsion is formed.

25. The method of any one of paragraphs 21 to 24, wherein the silicone oil includes a polydimethylsiloxane.

26. The method of paragraph 25, wherein the polydimethylsiloxane is a 5 cSt polydimethylsiloxane.

27. The method of any one of paragraphs 21 to 26, wherein the continuous phase includes octamethylcyclotetrasiloxane.

28. The method of paragraph 27, wherein the octamethylcyclotetrasiloxane is present at a concentration of about 0.1% to 2% by weight or about 0.5% by weight.

29. The method of any one of paragraphs 21 to 28, wherein the continuous phase includes a trimethylsiloxysilicate.

30. The method of paragraph 29, wherein the trimethyloxysiloxysilicate is present at a concentration of about 0.1% to 5% by weight.

31. The method of any one of paragraphs 21 to 30, wherein the silicone surfactant includes a silicone surfactant having a comb structure.

32. The method of any one of paragraphs 21 to 30, wherein the silicone surfactant includes a silicone surfactant having a di-block or tri-block structure.

33. The method of any of paragraphs 21 to 32, wherein the silicone surfactant is present at a concentration of about 0.2% to 5% by weight.

34. The method of paragraph 33, wherein the silicone surfactant is present at a concentration of about 0.5% to 2% by weight.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. A method of performing an assay, the method comprising:
   (A) forming an emulsion including aqueous droplets dispersed in a continuous phase, the aqueous droplets containing an analyte, the continuous phase including a silicone oil and a silicone surfactant, the silicone surfactant having the formula

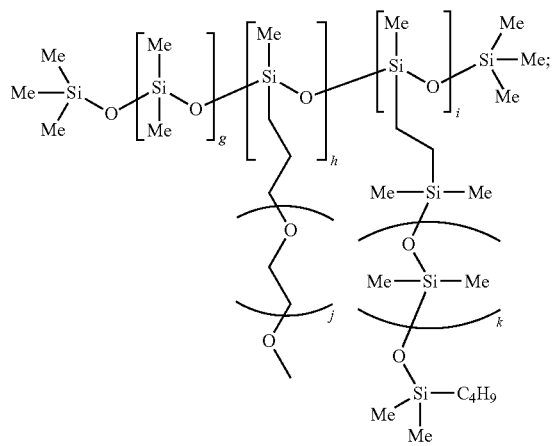

the formula

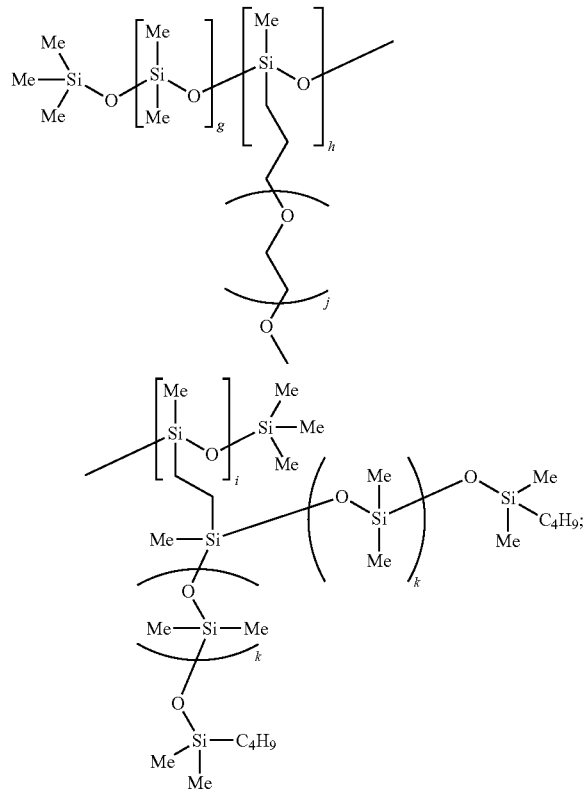

or the formula

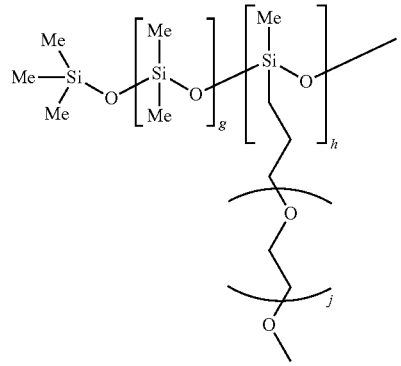

-continued

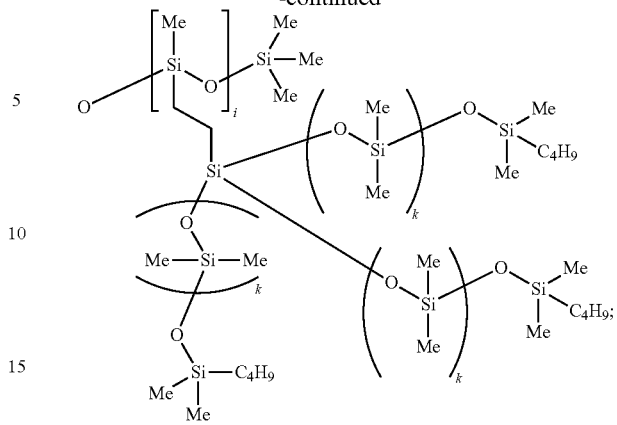

wherein
  each g is independently 5-200;
  each h is independently 1-5;
  each i is independently 1-5;
  each j is independently 15-50;
  each k is independently 2-100; and
  (B) detecting a signal related to the analyte from the aqueous droplets.

2. The method of claim 1, wherein only a subset of the aqueous droplets contains the analyte.

3. The method of claim 1, wherein the analyte is a nucleic acid.

4. The method of claim 1, wherein the step of detecting a signal includes a step of detecting light.

5. The method of claim 4, wherein the aqueous droplets contain a luminescent reporter, and wherein the step of detecting light includes a step of detecting light from the luminescent reporter.

6. The method of claim 5, wherein the luminescent reporter includes a dye-labeled probe.

7. The method of claim 5, wherein the luminescent reporter includes an intercalating dye.

8. The method of claim 1, further comprising a step of performing an enzyme-catalyzed reaction in the aqueous droplets.

9. The method of claim 1, wherein the silicone oil includes octamethyl trisiloxane, cyclopentasiloxane, or a trimethylsiloxysilicate at a concentration of about 0.1% to 5%.

10. The method of claim 1, wherein the silicone oil includes one or more of octamethyl trisiloxane and polydimethylsiloxane.

11. The method of claim 1, wherein the silicone surfactant is present in the continuous phase at a concentration of about 0.1% to 10% by weight.

* * * * *